(12) United States Patent
Pitner et al.

(10) Patent No.: US 7,951,605 B2
(45) Date of Patent: May 31, 2011

(54) MULTIANALYTE SENSOR

(75) Inventors: James Bruce Pitner, Durham, NC (US); Glenn Vonk, Fuquay-Varina, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1003 days.

(21) Appl. No.: 11/145,944

(22) Filed: Jun. 7, 2005

(65) Prior Publication Data
US 2006/0078908 A1    Apr. 13, 2006

Related U.S. Application Data

(60) Provisional application No. 60/577,931, filed on Jun. 9, 2004.

(51) Int. Cl.
*C12Q 1/68* (2006.01)
*G01N 33/53* (2006.01)

(52) U.S. Cl. ............... 436/95; 435/6; 435/7.1; 435/7.2; 435/14; 435/287.1; 435/287.2

(58) Field of Classification Search .............. 436/95; 435/6, 7.1, 7.2, 14, 287.1, 287.2
See application file for complete search history.

(56) References Cited

U.S. PATENT DOCUMENTS

| | | |
|---|---|---|
| 4,160,698 A | 7/1979 | Miyairi et al. |
| 4,269,941 A | 5/1981 | Ichimura |
| 4,452,892 A | 6/1984 | Rosevear |
| 4,703,756 A | 11/1987 | Gough et al. |
| 5,001,054 A | 3/1991 | Wagner |
| 5,165,407 A | 11/1992 | Bindra et al. |
| 5,200,334 A | 4/1993 | Dunn et al. |
| 5,226,902 A | 7/1993 | Bae et al. |
| 5,292,801 A | 3/1994 | Avnir et al. |
| 5,298,022 A | 3/1994 | Bernardi |
| 5,300,564 A | 4/1994 | Avnir et al. |
| 5,342,789 A | 8/1994 | Chick et al. |
| 5,436,161 A | 7/1995 | Bergstrom et al. |
| 5,445,920 A | 8/1995 | Saito |
| 5,501,836 A | 3/1996 | Myerson |

(Continued)

FOREIGN PATENT DOCUMENTS

EP           409033          4/1992

(Continued)

OTHER PUBLICATIONS

Abreu, M.S.C. et al., Binding of Fluorescent Lipid Amphiphile to Albumin and Its Transfer to Lipid Bilayer Membranes; Biophysical Journal, vol. 84: 386-399 (Jan. 2003).

(Continued)

*Primary Examiner* — Krishnan S Menon
*Assistant Examiner* — Rebecca Fritchman
(74) *Attorney, Agent, or Firm* — Morgan, Lewis & Bockius LLP

(57) ABSTRACT

The invention relates to devices for continuously measuring the concentrations of more than one target analyte. Specifically, the devices comprise a plurality of analyte binding domains, with each domain being capable of specifically and reversibly binding to at least one of the target analytes. The devices further comprise a membrane surrounding these binding domains that is permeable to the target analytes. The devices convey binding information to a detector. The invention also relates to methods of using the devices, including monitoring chronic disease states in an individual.

18 Claims, 4 Drawing Sheets

Trisensor Configurations

3 Binding Domains / 1 Polymer membrane / 1 Device

3 Binding Domains / 3 Polymer membranes / 1 Device

3 Binding Domains / 3 Polymer membranes / 3-Part Device

Polymer membrane

Binding Domain 1

Binding Domain 2

Binding Domain 3

U.S. PATENT DOCUMENTS

| | | | |
|---|---|---|---|
| 5,517,313 | A | 5/1996 | Colvin |
| 5,577,137 | A | 11/1996 | Churchill et al. |
| 5,650,311 | A | 7/1997 | Avnir et al. |
| 5,817,493 | A | 10/1998 | Reetz et al. |
| 5,824,526 | A | 10/1998 | Avnir et al. |
| 5,882,494 | A | 3/1999 | Van Antwerp |
| 5,894,351 | A | 4/1999 | Colvin |
| 5,910,661 | A | 6/1999 | Colvin |
| 6,016,689 | A | 1/2000 | Bright et al. |
| 6,080,402 | A | 6/2000 | Reetz et al. |
| 6,197,534 | B1 | 3/2001 | Lakowicz et al. |
| 6,277,627 | B1 | 8/2001 | Hellinga |
| 6,288,214 | B1 | 9/2001 | Hook et al. |
| 6,319,852 | B1 | 11/2001 | Smith et al. |
| 6,403,337 | B1 | 6/2002 | Bailey et al. |
| 6,432,723 | B1 | 8/2002 | Plaxco et al. |
| 6,455,222 | B1 | 9/2002 | Fukino et al. |
| 6,462,162 | B2 | 10/2002 | Van Antwerp |
| 6,475,750 | B1 | 11/2002 | Han et al. |
| 6,495,352 | B1 | 12/2002 | Brinker et al. |
| 6,497,729 | B1 | 12/2002 | Moussy et al. |
| 6,521,446 | B2 | 2/2003 | Hellinga |
| 6,751,491 | B2 | 6/2004 | Lew et al. |
| 7,122,378 | B1 * | 10/2006 | Akita et al. ............... 436/94 |
| 2002/0004217 | A1 | 1/2002 | Hellinga |
| 2002/0142347 | A1 * | 10/2002 | Knudsen et al. ........... 435/7.1 |
| 2002/0182600 | A1 * | 12/2002 | Smith ............................ 435/6 |
| 2003/0100822 | A1 * | 5/2003 | Lew et al. .................. 600/365 |
| 2003/0153026 | A1 | 8/2003 | Alarcon et al. |
| 2004/0005582 | A1 * | 1/2004 | Shipwash ...................... 435/6 |
| 2004/0234962 | A1 | 11/2004 | Alarcon et al. |
| 2005/0042704 | A1 | 2/2005 | Alarcon et al. |
| 2005/0112685 | A1 | 5/2005 | Amiss et al. |

FOREIGN PATENT DOCUMENTS

| | | |
|---|---|---|
| EP | 775669 B1 | 5/2001 |
| JP | 60159643 | 8/1987 |
| JP | 4215054 | 3/1992 |
| JP | 60029657 | 8/1992 |
| JP | 2248852 | 12/1997 |
| JP | 2120655 | 1/1998 |
| WO | WO 94/27137 A | 11/1994 |
| WO | WO 00/59370 | 10/2000 |
| WO | WO 01/16575 A | 3/2001 |
| WO | WO 00/13003 A | 3/2003 |
| WO | WO 2004/039487 A | 5/2004 |

OTHER PUBLICATIONS

Civelek, V.N. et al., Intracellular pH in Adipocytes: Effects of Free Fatty Acid Diffusion across the Plasma Memebrane, Lipolytic Agonists, and Insulin; Proc. Natl. Acad. Sci. (USA), vol. 93: 10139-10144 (Sep. 1996).
De Lorimier, R.M. et al., Construction of a Fluorescent Biosensor Family; Protein Science, vol. 11: 2655-2675 (Nov. 2002).
Hermanson, Bioconjugate Techniques, pp. 531-533; Academic Press, San Diego, CA, USA (1996).
Looger, L.L. et al., Computational Design of Receptor and Sensor Proteins with Novel Functions; Nature, vol. 423(6939): 185-190 (May 2003).
McArthur. M.J. et al., Cellular Uptake and Intracellular Trafficking of Long Chain Fatty Acids; J. Lipid. Res., vol. 40: 1371-1383 (Aug. 1999).
Quinn C.A.P. et al., Biocompatible Glucose-Permeable Hydrogel for in situ Coating of Implantable Biosensors; Biomaterials, vol, 18: 1665-1670 (Dec. 1997).
Ratner, B.D. and Hoffman, A.S., "Thin Films, Grafts, and Coatings" Chapter 2, in "Biomaterials Science: An Introduction to Materials in Medicine", B.D. Ratner, A.S. Hoffman, F.J. Shoen, J.E. Lemons, Eds., Academic Press, San Diego, CA, 1996, pp. 105-117.
Rattan, S.I.S. et al., Protein Synthesis, Posttranslational Modifications and Againg; Annals N.Y. Acad. Sci., vol. 663: 48-62 (Nov. 1992).
Richieri, G.V. et al., A Fluorescently Labeled Intestinal Fatty Acid Binding Protein; J. Biol. Chem., vol. 267(33): 23495-23501 (Nov. 1992).
Seifter S. and Englard, S., Analysis for Protein Modificaitons and Nonprotein Cofacotrs; Methods in Enzymology, vol. 182: 626-646 (1990).
Smith, E.R. and Storch, J., The Adipocyte Fatty Acid-binding Protein Binds to Membranes by Electrostatic Interacitons; J. Biol. Chem., vol. 274(50): 35325-35330 (Dec. 1999).
Weisiger, R.A., Saturable Stimulation of Fatty Acid Transport Through Model Cytoplasm by Soluble Binding Protein; Am. J. Physiol., vol. 277: 109-119 (Jul. 1999).
Wold, F., "Posttranslational Protein Modifications: Perspectives and Prospectives" in Posttranslational Covalent Modification of Proteins, Johnson, B., Ed., pp. 1-17; Academic Press, New York, NY, USA (1983).
Bhatia et al., Optical Fiber Long-Period Grating Sensors, Optics Letters (1996) 21:692-694.
Blair et al., Fiber Optic Sensor for Ca2+ Based on Induced Change in the Conformation of the Protein Calmodulin., Anal. Chem., (1994) 66: 300-02.
Chen et al., A poly(N-isopropylacrylamide-co-N-acryloxysuccinimide-co-2-hydroxyethyl methacrylate) composite hydrogel . . . ,Enzyme and Microbial Technologyy, 2000, 26: 359-367.
Galan-Vidal et al., Glucose Biosensor Based on a Reagentless Graphite-Epoxy Screen-Printable Biocomposite. Sensors and Actuators, B: Chemical, 1997, B45: 55-62.
Gautier et al. Reagentless Bioluminescent Sensor for NADH, Analytical Letters, 1994 27: 2055-2069.
Gautier et al., Cofactor-containing bioluminescent fibre-optice sensor: new developments with poly(vinyl alchohol) matrices, Analytica Chimica Acta, 255 (1991) 253-258.
Govind, R., Protein Engineered Glucose Sensor, Database FEDRIP on Dialog (R) File 26:, NTIS, 00352410, Identifying No. 1R01RR14170-01, Abstract 1998.
Gowada et al., Development of an Implantable Skin Port Sensor for Use as an In-Vivo Optical Glucose Sensing Platform, SPIE 2001 4263: 11-19.
Gilardi et al., Engineering the Maltose Binding Protein for Reagentless Fluorescence Sensing., Anal. Chem., 1994 66 (21): 3840-3847.
Gruber et al., Preparation of Thiol-Reactive Cy5 Derivatives from Commercial Cy5 Succinimidyl Ester, Bioconjugate Chem., 2000 11: 161-166.
Ishihara et al., Glucose Induced Permeation Control of Insulin Through a Complex Membrane Consisting of Immobilized Glucose Oxidase, Polymer J., 1984 16:625.
Kermis et al., Transport properties of pHEMA membranes for optical glucose affinity sensors, J. Membrane Science, 2002 5456:1-12.
Kok et al., Immobilization of acetylcholinestesterase and choline oxidase in/on pHEMA membrane for biosensor construction, J. Biomater. Sci. Polymer Edn., 2001 12:1161-76.
Liu et al., Reagentless amperometric biosensors sensitive to hydrogen peroxide, glucose and lactose based on n-methyl phenazine . . . Analytica Chimica Acta, 1997 344:187-199.
Looger et al., Computational design of receptor and sensor proteins with novel functions, Nature 2003 423: 185-190.
Marvin et al., Engineering Biosensors by Introducing Fluroescent Allosteric Signal Transducers: Construction of a Novel Glucose Sensor, J. Am. Chem. Soc. 1998, 120, 7-11.
Meadows et al., Fiber-optic biosensors based on fluorescence energy transfer. Talanta, 1998 35: 145-150.
Mowbray et al., Structure of the periplasmic glucose/galactose receptor of *Slamonella typhimurium*, Receptor 1990 1:41-54.
O'Neal et al., Implantable biosensors: analysis of fluorescent light propagation through skin. Proc. SPIE 2001 4263: 20-24.
Quinn et al., Biocompatible, glucose-permeable hydrogel for in-situ coating of implantable biosensors, Biomaterials: 1997 18: 1665-70.
Quinn et al., Photo-crosslinked copolymers of 2-hydroxyethyl methacrylate, poly(ethylene glycol) tetra-acrylate and ethylene dimethacrylate . . . , Biomaterials, 1995 16:389-396.
Russell et al., A Fluorescence-based glucose biosensor using concanavalin A and Dextran encapsulated in a poly(ethylene glycol) hydrogel, Anal. Chem., 1999, 71: 3126-32.
Salins et al., A Novel Reagentless Sensing System for Measuring Glucose Based on the Galactose/Glucose-Binding Protein, Analytical Biochemistry, 2001, 19-26, vol. 294.

Sampath et al., Renewable, Reagentless Glucose Sensor Based on a Redox Modified Enzyme and Carbon-Silica Composite., Electroanalysis, 1996, 8: 1112-1116.

Tolosa et al., Glucose Sensor for Low-Cost Lifetime-Based Sensing Using a Genetically Engineered Protein, 1999, 114-120, vol. 267.

Topoglidis et al., Protein Adsorption and Nanocrystalline TiO2 Films: An Immobilization Strategy for Bioanalytical Devices, Analytical Chemistry, 1998, 70: 5111-5113.

Vyas et al., Sugar and Signal-Transducer Binding Sites of the *Escherichia coli* Galactose Chemoreceptor Protein, Science, 1998, 242: 1290-95.

Wenner et al., Genetically Designed Biosensing Systems for High-Throughput Screening of Pharma . . . Advances in Fluorescence Sensing Technology V, SPIE vol. 4252, 2001, 59-70.

Gerritsen et al., Biocompatibility Evaluation of Sol-Gel Coatings for Subcutaneously Implantable Glucose Sensors, Biomaterials 2000, 21, 71-78.

Gill et al., Novel Sol-Gel Matrices for the Immobilization of Enzymes, Ann N Y Acad Sci., 1996, 799, 697-700.

Flora et al., Effect of Matrix Aging on the Behavior of Human Serum Albumin Entrapped in a Tetraethyl Orthosilicate-Derived Glass, Chemistry of Materials 2001,13, 4170-4179.

Brennan, Preparation and Entrapment of Fluorescently Labeled Proteins for the Development of Reagentless Optical Biosensors, Journal of Fluorescence 1999, 9, 295-312.

Flora et al., The Effect of Preparation and Aging Conditions on the Internal Environ. of Sol-Gel Derived Mater . . . , Can. Jrnl. of Chem.—Revue Can. De Chimie 1999, 77, 1617-25.

Zheng et al., Improv. the Performance of a Sol-Gel-Entrapped Metal-Binding Protein by Maximizing Protein Thermal Stability Before Entrapment, Chem. of Mat., 1998,10, 3974-3983.

Flora et al., Fluorometric Detection of Ca2+ Based on an Induced Change in the Conformation of Sol-Gel Entrapped Parvalbumin, Anal. Chem. 1998, 70, 4505-4513.

Zheng et al., Measurement of Intrinsic Fluorescence to Probe the Conformational Flexibility and Thermodynamic Stability of a Single . . . ,Matrix. Analyst 1998, 123, 1735-1744.

Dunn et al., Sensors Based on Sol-Gel Encapsulation Methods, Abstracts of Papers of the American Chemical Society 2001, 221, 473-COLL.

Narang et al., Glucose Biosensor Based on a Sol-Gel Derived Platform, Analy. Chem. 1994, 66, 3139-3144.

Baker et al., Effects of Poly(Ethylene Glycol) Doping on the Behavior of Pyrene Rhodamine 6g, and Acrylodan-Labeled . . . , Jrnl. of Sol-Gel Science and Technology 1998, 11, 43-54.

Dave et al., Encapsulation of Proteins in Bulk and Thin Film Sol-Gel Matrices, Journal of Sol-Gel Science and Technology 1997, 8, 629-634.

Zusman et al., Doped Sol-Gel Glasses As Chemical Sensors, J. Non-Crystalline Solids, 1990, 122, 107-109.

Avnir et al., Enzymes and Other Proteins Entrapped in Sol-Gel Materials, Chemistry of Materials 1994, 6, 1605-1614.

Avnir et al., Encapsulation of Organic-Molecules and Enzymes in Sol-Gel Glasses . . . , ACS Symposium Series 1992, 499, 384-404.

Gill et al., Encapsul. of Biologicals Within Silicate, Siloxane, and Hybrid Sol-Gel Polymers: Efficient and Generic Approach, Jrnl. of the Amer. Chem. Soc. 1998, 120, 8587-98.

Flora et al., Comparison of Formats for the Development of Fiber-Optic Biosensors Utiliz. Sol-Gel Derived Mat. Entrapping Fluorescently-Labelled . . . , Analyst 1999, 124, 1455-62.

Zheng et al., Measurement of Fluorescence From Tryptophan to Probe the Environ. and Reaction Kinetics Within Protein-Doped Sol-Gel Derived . . . , Anal. Chem. 1997, 69, 3940-3949.

Lev et al., Organically Modified Sol-Gel Sensors, Analytical Chem., 1995, 67, A-22-A30.

Shtelzer et al., An Optical Biosensor Based Upon Glucose-Oxidase Immobilized in Sol-Gel Silicate Matrix, Biotechnology and Applied Biochemistry 1994, 19, 293-305.

Beach et al., Subminiature Implantable Potentiostat and Modified Commercial Telemetry Device for Remote Glucose Monit., IEEE Trans. on Instru. and Measure., 1999, 48, 1239-45.

Braun et al., Biochemically Active Sol-Gel Glasses: The Trapping of Enzymes, Materials Letters 1990, 10, 1-5.

Zhao et al., Novel Degradable Poly(ethylene glycol) Hydrogel for Controlled Release of Protein, J. Pharm. Sci., 1998 87: 1450-58.

Rospert M., Multianalyte sen. for the simult. determin. of glucose, L-lactate and uric acid based on a microelectrode array, Sen. and Actuators, vol. 43, No. 1, 1997 pp. 87-93.

Petrou P., Microdevice with integrated dialysis probe and biosensor array for continuous multi-analyte monit., Biosensors and Bioelectronics, vol. 18, No. 5-6, 2003, pp. 613-619.

Orban M., Kinetic anal. of immuno. with coval. immobilized fatty acid-binding protein using a grating coupler sen., Jrnl. of Immunological Meth. vol. 215, No. 1 1998, pp. 17-26.

Wadum Majken, Fluorescently labelled bovine acyl-CoA-binding protein acting as an acyl-CoA sensor: Interaction with CoA and acyl-CoA esters and its use in measuring free acyl-CoA esters and non-esterified fatty acids, Biochemical Journal, vol. 365, No. 1, Jul. 1, 2002, pp. 165-172.

International Search Report for PCT/US2005/019778 dated Oct. 5, 2005.

Frebel et al., Multianalyte sensor for the simultaneous determination of glucose, L-lactate and uric acid based on a microelectrode array, Sensors and Actuators B43 1997 87-93.

International Preliminary Report on Patentability for PCT/US2005/019778 dated Dec. 14, 2006.

* cited by examiner

Trisensor Configurations

3 Binding Domains / 1 Polymer membrane / 1 Device

3 Binding Domains / 3 Polymer membranes / 1 Device

3 Binding Domains / 3 Polymer membranes / 3-Part Device

Polymer membrane

Binding Domain 1

Binding Domain 2

Binding Domain 3

MULTIANALYTE SENSOR

This application claims priority to U.S. Provisional Application No. 60/577,931, filed Jun. 9, 2004.

BACKGROUND OF THE INVENTION

1. Field of the Invention

The invention relates to devices for continuously measuring the concentrations of more than one target analyte. Specifically, the devices comprise a plurality of analyte binding domains, with each domain being capable of specifically and reversibly binding to at least one of the target analytes. The devices further comprise a membrane surrounding these binding domains that is permeable to the target analytes. The devices convey binding information to a detector. The invention also relates to methods of using the devices, including monitoring chronic disease states in an individual.

2. Background of the Invention

Glucose is the most monitored energy metabolite for diagnosis and management of diabetes today. Indeed, maintaining blood glucose within the "normal" range of 70 to 120 mg/dL using intensive insulin therapy, and increased glucose monitoring, can significantly improve the long-term health of diabetes patients. While incremental advances have steadily been made in glucose monitor performance, most of the monitors available today still require the extraction of blood from patients, and the analysis of glucose levels by a separate monitor. The limitations of this technology are well known (pain, inconvenience, and non-compliance, primarily). Furthermore, current reaction-based sensors typically rely on an enzymatic reaction that may include cofactors, mediators, reactive products (e.g., hydrogen peroxide), or co-substrates (e.g., oxygen), which often complicates sensor development and performance analysis. A more desirable sensor, from a subject's and physician's point of view, would be a more reliable device that is not subject to numerous complications, as well as a device that has a long in vivo lifetime, is capable of quantitatively assessing glucose concentration at regular (short) intervals, and requires a minimal number of calibrations using finger-prick blood samples.

While monitoring glucose is critical for the survival of anyone with diabetes, glucose levels alone provide insufficient data for understanding the complex and dynamic metabolic processes underlying this disease and its development. While glucose is the primary energy-generating metabolite used by the brain, the majority of a day's energy is generated by tissue metabolism of fatty acids. Hence, real-time monitoring of both glucose and fatty acid levels provides greater information on one's metabolic state and will likely be important for understanding and normalizing metabolism. Fatty acid monitoring may be particularly important for understanding the events leading to early development of a pre-diabetic state or insulin resistance, particularly in Type 2 diabetes.

Similarly, minimally invasive metabolite monitors could be desirable for other applications, such as monitoring the fatigue levels in athletes or soldiers. Indeed, exercise also impacts a subjects metabolic state, and lactate, a by-product of moderate to intense exercise, acts as a marker for energy expenditure as well as exercise burden. Hence, changes in lactate concentration signify alterations in glucose metabolism as well. Coordinated use of glucose, lactate, and fatty acid sensors could therefore lead to devices that more precisely monitor fatigue and exhaustion. Continued monitoring of multiple metabolites for example, would allow athletes or soldiers to maintain improved readiness and decrease recovery times after exertion.

Currently, there is no sensor that continuously monitors in vivo metabolites. Furthermore, of the single-metabolite sensors currently available, none measure more than one metabolite directly. Accordingly, there is a need in the art for a sensor that monitors multiple metabolites and does so in a minimally invasive or painful manner. Further, the multianalyte biosensor should be designed such that it is free of complications, such as enzyme by-products.

SUMMARY OF THE INVENTION

The invention relates to devices for continuously measuring the concentrations of more than one target analyte. Specifically, the devices comprise a plurality of analyte binding domains, with each domain being capable of specifically and reversibly binding to at least one of the target analytes. The devices further comprise a membrane surrounding these binding domains that is permeable to the target analytes. The devices convey binding information to a detector. The invention also relates to methods of using the devices, including monitoring chronic disease states in an individual.

DETAILED DESCRIPTION OF THE INVENTION

Figure 1:
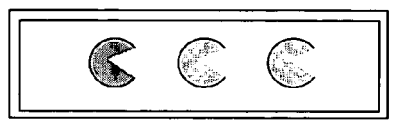
FIG. 1 depicts several embodiments of multianalyte sensor designed for monitoring three analytes.
Figure 1:
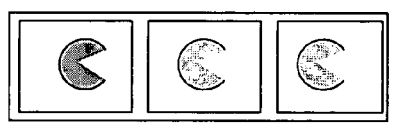
Figure 1:
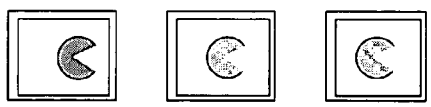
Figure 1:
Figure 1:
Figure 1:
Figure 1:

The invention relates to devices for continuously measuring the concentrations of more than one target analyte. Specifically, the devices comprise a plurality of analyte binding domains, with each domain being capable of specifically and reversibly binding to at least one of the target analytes. The devices further comprise a membrane surrounding these binding domains that is permeable to the target analytes. The devices convey binding information to a detector. The invention also relates to methods of using the devices, including monitoring chronic disease states in an individual.

The devices of the present invention can be used as biosensors. The biosensors of the present invention retain the binding domains by physical entrapment or immobilization in a manner that does not interfere with the domains' conformational change upon target analyte binding. Second, the sensor allows efficient diffusion of the analytes so it can produce a quantifiable signal from its equilibration with the domains. The sensor components also produce minimal or no background signal such that the signal is compatible with the detection protocols, e.g. optical fibers or surface plasmon resonance. The sensor also provides sufficient structural and mechanical stability to insure its performance during the course of its storage and subsequent in vivo use. Lastly, the sensor must be as safe and as biocompatible as possible for continuous in vivo use.

The devices of the current invention can be used to assess or measure the concentrations of more than one target analytes. As used herein, concentration is used as it is in the art. The concentration may be expressed as a qualitative value, or more likely as a quantitative value. As used herein, the quantification of the analytes can be a relative or absolute quantity. Of course, the quantity (concentration) of any of the analytes may be equal to zero, indicating the absence of the particular analyte sought. The quantity may simply be the measured signal, e.g., fluorescence, without any additional measurements or manipulations. Alternatively, the quantity may be expressed as a difference, percentage or ratio of the measured value of the particular analyte to a measured value of another compound including, but not limited to, a standard or another analyte. The difference may be negative, indicating a decrease in the amount of measured analyte(s). The quantities may also be expressed as a difference or ratio of the analyte(s) to itself, measured at a different point in time. The quantities of analytes may be determined directly from a generated signal, or the generated signal may be used in an algorithm, with the algorithm designed to correlate the value of the generated signals to the quantity of analyte(s) in the sample.

The devices of the current invention are designed to possess capabilities of continuously measuring the concentrations of more than one analyte. Of course, "more than one" includes, but is not limited to, two, three, four, five, six, seven, eight, nine and ten or more analytes. As used herein, the term "continuously," in conjunction with the measuring of an analyte, is used to mean the device either generates or is capable of generating a detectable signal at any time during the life span of the device. The detectable signal may be constant in that the device is always generating a signal, even if the signal is not detected. Alternatively, the device may be used episodically, such that a detectable signal may be generated, and detected, at any desired time.

The target analytes can be any molecule or compound where the concentration is desired to be measured. In one embodiment, the target analytes are not labeled. While not a requirement of the present invention, the device is particularly useful in an in vivo setting for measuring target analytes as they occur or appear in a subject. As such, the target analytes need not be labeled. Of course, unlabeled target analytes may also be measured in an in vitro or in situ setting as well. In another embodiment, the target analytes may be labeled. Labeled target analytes can be measured in an in vivo, in vitro or in situ setting.

Examples of classes of analytes that can be measured include, but are not limited to amino acids, peptides, polypeptides, proteins, carbohydrates, lipids, nucleotides, oligonucleotides, polynucleotides, glycoproteins or proteoglycans, lipoproteins, lipopolysaccharides, drugs, drug metabolites, small organic molecules, inorganic molecules and natural or synthetic polymers. As used herein, "carbohydrate" includes, but is not limited to monosaccharides, disaccharides, oligosaccharides and polysaccharides. "Carbohydrate" also includes, but is not limited to, molecules comprising carbon, hydrogen and oxygen that do not fall within the traditional definition of a saccharide—i.e., an aldehyde or ketone derivative of a straight chain polyhydroxyl alcohol, containing at least three carbon atoms. Thus, for example, a carbohydrate may contain fewer than three carbon atoms. As used herein, the term "lipid" is used it is in the art, i.e., substances of biological origin that are made up primarily or exclusively of nonpolar chemical groups such that they are readily soluble in most organic solvents, but only sparingly soluble in aqueous solvents. Examples of lipids include, but are not limited to, fatty acids, triacylglycerols, glycerophospholipids, sphingolipids, cholesterol, steroids and derivatives thereof. For example, "lipids" include but are not limited to, the ceramides, which are derivatives of sphingolipids and derivatives of ceramides, such as sphingomyelins, cerebrosides and gangliosides. "Lipids" also include, but are not limited to, the common classes of glycerophospholipds (or phospholipids), such as phosphatidic acid, phosphatidylethanolamine, phosphatidylcholine, phosphatidylserine, phosphatidylinositol, phosphatidylglycerol and the like. As used herein, a "drug" can be a known drug or a drug candidate, whose activity or effects on a particular cell type are not yet known. A "drug metabolite" is any of the by-products or the breakdown products of a drug that is changed chemically into another compound or compounds. As used herein, "small organic molecule" includes, but is not limited to, an organic molecule or compound that does not fit precisely into other classifications highlighted herein.

In one embodiment, all of the target analytes are of the same class of compounds, e.g., proteins, or fatty acids or carbohydrates. In another embodiment, at least one of the target analytes is in a different compound class from the other target analytes. For instance, the device can measure a protein or polypeptide and a carbohydrate or carbohydrates. In yet another embodiment of the present invention, none of the target analytes are in the same class of compounds. Furthermore, the target analytes may be specific compounds within a class of compounds, e.g., glucose, palmitate, stearate, oleate, linoleate, linolenate, and arachidonate. Alternatively, the target analytes may be an entire class of compounds, or a portion or subclass thereof, e.g., fatty acids. Specific examples of target analytes include, but are not limited to, glucose, free fatty acids, lactic acid, C-reactive protein and anti-inflammatory mediators, such as cytokines, eicosanoids, or leukotrienes. In one embodiment, the target analytes are fatty acids, C-reactive protein, and leukotrienes. In another embodiment, the target analytes are glucose, lactic acid and fatty acids.

"Fatty acids," as used herein include all fatty acids, including free fatty acids (FFA) and fatty acids esterified to other molecules. Examples of specific fatty acids include, but are not limited to, palmitate, stearate, oleate, linoleate, linolenate, and arachidonate. The term "free fatty acid" is used herein as it is in the art in that FFA are not part of other molecules such as triglycerides or phospholipids. Free fatty acids also include non-esterified fatty acids that are bound to or adsorbed onto albumin. As used herein, the term "unbound free fatty acid" (unbound FFA) is used to denote a free fatty acid or free fatty acids that are not bound or adsorbed onto albumin or other serum proteins. In fact, it is believed that unbound FFA circulate in low levels in the body. (See McArthur M. J., et al., *J. Lipid Res.*, 40: 1371-1383, (1999), the entirety of which is hereby incorporated by reference.) Furthermore, there is also evidence that an equilibrium between albumin-bound free fatty acids and unbound free fatty across cell membranes exists and is readily established. For example, unbound FFA can diffuse across from an adipose cell onto albumin, where the FFA is transported to other tissues. The albumin-bound FFA then diffuses across the cell membrane of another cell where the FFA can be stored or used as an energy source. (See Abreu, M. S. C., et al., *Biophys. J.*, 84: 386-399, (2003), and Weisiger, R. A., *Am. J. Physiol-Gastr.*, 277: G109-G119, (1999), the entireties of which are hereby incorporated by reference.)

The devices of the current invention comprise a plurality of binding domains. As used herein, "plurality" is more than one, including but not limited to, two, three, four, five, six, seven, eight, nine and ten or more. A "binding domain" is used herein as it is in the art. Namely, a binding domain is molecule that binds a target in an specific manner. The binding domain may comprise an entire molecule, or a portion thereof. As used herein, a "binding entity" is the molecule or compound comprising the binding domain or domains. The binding entities or binding domains may be immobilized directly onto a solid support, such as a glass slide. The may be immobilized directly onto or into a hydrogel or sol-gel. Other surfaces include, but are not limited to optical fibers, waveguides or etched gratings on silicon or glass, plasma-treated polystyrene, modified metal surfaces, including thiolated gold. Alternatively, they may not be directly immobilized. Example of binding entities include, but are not limited to polypeptides and proteins. In one embodiment of the current invention, the binding entity comprises a single polypeptide or protein. The single polypeptide or protein comprises the plurality of binding domains, such that all of the binding domains of the device are within a single protein or polypeptide chain. In another embodiment, more than one binding entity comprise a plurality of proteins or polypeptides. This plurality of proteins or polypeptides comprise the plurality of binding domains. In particular, one binding domain may be present on one protein or polypeptide.

In general, the binding domain will, but not necessarily, correspond to the number of target analytes in a one to one fashion. In this embodiment, the device comprises only one binding domain per target analyte. In another embodiment, the device comprises more than one binding domain per target analyte.

In one embodiment of the present invention, the binding entities comprise polypeptides or proteins. In particular, the proteins comprising the binding domains include, but are not limited to periplasmic binding proteins (PBPs). As used herein a PBP is a protein characterized by its three-dimensional configuration (tertiary structure), rather than its amino acid sequence (primary structure) and is characterized by a lobe-hinge-lobe region. The PBP will normally bind an analyte specifically in a cleft region between the lobes of the PBP. Furthermore, the binding of an analyte in the cleft region will then cause a conformational change to the PBP that makes detection of the analyte possible. Periplasmic binding proteins of the current invention include any protein that possesses the structural characteristics described herein; and analyzing the three-dimensional structure of a protein to determine the characteristic lobe-hinge-lobe structure of the PBPs is well within the capabilities of one of ordinary skill in the art. Examples of PBPs include, but are not limited to, glucose-galactose binding protein (GGBP), maltose binding protein (MBP), ribose binding protein (RBP), arabinose binding protein (ABP), dipeptide binding protein (DPBP), glutamate binding protein (GluBP), iron binding protein (FeBP), histidine binding protein (HBP), phosphate binding protein (PhosBP), glutamine binding protein (QBP), oligopeptide binding protein (OppA), or derivatives thereof, as well as other proteins that belong to the families of proteins known as periplasmic binding protein like I (PBP-like I) and periplasmic binding protein like II (PBP-like II). The PBP-like I and PBP-like II proteins have two similar lobe domains comprised of parallel β-sheets and adjacent α helices. The glucose-galactose binding protein (GGBP) belongs to the PBP-like I family of proteins, whereas the maltose binding protein (MBP) belongs to the PBP-like II family of proteins. The ribose binding protein (RBP) is also a member of the PBP family of proteins. Other non-limiting examples of periplasmic binding proteins are listed in Table I.

TABLE I

Genes Encoding Common Periplasmic Binding Proteins

| Gene name | Substrate | Species |
|---|---|---|
| alsB | Allose | E. coli |
| araF | Arabinose | E. coli |
| AraS | Arabinose/fructose/xylose | S. solfataricus |
| argT | Lysine/arginine/ornithine | Salmonella typhimurium |
| artI | Arginine | E. coli |
| artJ | Arginine | E. coli |
| b1310 | Unknown (putative, multiple sugar) | E. coli |
| b1487 | Unknown (putative, oligo-peptide binding) | E. coli |
| b1516 | Unknown (sugar binding protein homolog) | E. coli |
| butE | vitamin B12 | E. coli |
| CAC1474 | Proline/glycine/betaine | Clostridium acetobutylicum |
| cbt | Dicarboxylate (Succinate, malate, fumarate) | E. coli |
| CbtA | Cellobiose | S. solfataricus |
| chvE | Sugar | A. tumefaciens |
| CysP | Thiosulfate | E. coli |
| dctP | C4-dicarboxylate | Rhodobacter capsulatus |
| dppA | Dipeptide | E. coli |
| FbpA | Iron | Neisseria gonorrhoeae |
| fecB | Fe(III)-dicitrate | E. coli |
| fepB | enterobactin-Fe | E. coli |
| fhuD | Ferrichydroxamate | E. coli |
| FliY | Cystine | E. coli |
| GlcS | glucose/galactose/mannose | S. solfataricus |
| glnH (protein: GLNBP) | Gluconate | E. coli |
| gntX | Gluconate | E. coli |
| hemT | Haemin | Y. enterocolitica |
| HisJ (protein: HBP) | Histidine | E. coli |
| hitA | Iron | Haemophilus influenzae |
| livJ | Leucine/valine/isoleucine | E. coli |
| livK (protein: L-BP) | Leucine | E. coli |
| malE (protein: MBP) | maltodextrin/maltose | E. coli |
| mglB (protein: GGBP) | glucose/galactose | E. coli |
| modA | Molybdate | E. coli |
| MppA | L-alanyl-gamma-D-glutamyl-meso-diaminopimelate | E. coli |
| nasF | nitrate/nitrite | Klebsiella oxytoca |
| nikA | Nickel | E. coli |
| opBC | Choline | B. Subtilis |
| OppA | Oligopeptide | Salmonella typhimurium |
| PhnD | Alkylphosphonate | E. coli |
| PhoS (Psts) | Phosphate | E. coli |
| potD | putrescine/spermidine | E. coli |
| potF | Polyamines | E. coli |
| proX | Betaine | E. coli |
| rbsB | Ribose | E. coli |
| SapA | Peptides | S. typhimurium |
| sbp | Sulfate | Salmonella typhimurium |
| TauA | Taurin | E. coli |
| TbpA | Thiamin | E. coli |
| tctC | Tricarboxylate | Salmonella typhimurium |
| TreS | Trehalose | S. solfataricus |
| tTroA | Zinc | Treponema pallidum |
| UgpB | sn-glycerol-3-phosphate | E. coli |
| XylF | Xylose | E. coli |
| YaeC | Unknown (putative) | E. coli |

TABLE I-continued

Genes Encoding Common Periplasmic Binding Proteins

| Gene name | Substrate | Species |
|---|---|---|
| YbeJ(Gltl) | glutamate/aspartate (putative, super-family: lysine-arginine-ornithine-binding protein) | E. coli |
| YdcS(b1440) | Unknown (putative, spermidine) | E. coli |
| YehZ | Unknown (putative) | E. coli |
| YejA | Unknown (putative, homology to periplasmic oligo-peptide-binding protein - Helicobactr pylori) | E. coli |
| YgiS (b3020) | Oligopeptides (putative) | E. coli |
| YhbN | Unknown | E. coli |
| YhdW | Unknown (putative, amino acids) | E. coli |
| YliB (b0830) | Unknown (putative, peptides) | E. coli |
| YphF | Unknown (putative sugars) | E. coli |
| Ytrf | Acetoin | B. subtilis |

Other examples of proteins that may comprise the binding domains include, but are not limited to intestinal fatty acid binding proteins (FAPBs). The FABPs are a family of proteins that are expressed at least in the liver, intestine, kidney, lungs, heart, skeletal muscle, adipose tissue, abnormal skin, adipose, endothelial cells, mammary gland, brain, stomach, tongue, placenta, testis, retina. The family of FABPs is, generally speaking a family of small intracellular proteins (~14 kDa) that bind fatty acids and other hydrophobic ligands, through non-covalent interactions. See Smith, E. R. and Storch, J., *J. Biol. Chem.*, 274 (50):35325-35330 (1999), which is hereby incorporated by reference in its entirety. Members of the FABP family of proteins include, but are not limited to, proteins encoded by the genes FABP1, FABP2, FABP3, FABP4, FABP5, FABP6, FABP7, FABP(9) and MP2. Proteins belonging to the FABP include I-FABP, L-FABP, H-FABP, A-FABP, KLBP, mal-1, E-FABP, PA-FABP, C-FABP, S-FABP, LE-LBP, DA11, LP2, Melanogenic Inhibitor, to name a few.

In one embodiment of the present invention, GGBP, a FABP and a GGBP derivative comprise the binding domains. In particular, the FABP is I-FABP. As used herein, a "derivative" of a protein or polypeptide is a protein or polypeptide that shares substantial sequence identity with the wild-type protein. Examples of derivative proteins include, but are not limited to, mutant and fusion proteins. A "mutant protein" is used herein as it is in the art. In general, a mutant protein can be created by addition, deletion or substitution of the wild-type primary structure of the protein or polypeptide. Mutations include for example, the addition or substitution of cysteine groups, non-naturally occurring amino acids, and replacement of substantially non-reactive amino acids with reactive amino acids.

The mutant proteins may be mutated to bind more than one analyte in a specific manner. Indeed, the mutant proteins may possess specificity towards its wild-type analyte and another target ligand.

Likewise, the mutant proteins may be able to only bind an analyte or analytes that the wild-type binding protein does not bind. Methods of generating mutant proteins are well-known in the art. For example, Looger, et al., (*Nature* 423 (6936): 185-190 (2003)), which is hereby incorporated by reference, disclose methods for re-designing binding sites within periplasmic binding proteins that provide new analyte-binding properties for the proteins. These mutant binding proteins retain the ability to undergo conformational change, which can produce a directly generated signal upon analyte-binding. By introducing between 5 and 17 amino acid changes, Looger, et al. constructed several mutant proteins, each with new selectivities for TNT (trinitrotoluene), L-lactate, or serotonin. For example, Looger et al. generated L-lactate binding proteins from ABP, GGBP, RBP, HBP and QBP. In one embodiment, the device comprises GGBP specific for glucose, a FABP specific for fatty acids, and a GGBP derivative where the GGBP derivative specifically binds L-lactate. In this embodiment, the target analytes are indeed glucose, fatty acids and L-lactate. In another embodiment, the device comprises a FABP specific for fatty acid and GGBP or a GGBP derivative, specific for glucose. In yet another embodiment, the device comprises a GGBP or GGBP derivative specific for glucose and a GGBP derivative specific for L-lactate. Table II lists other mutations to GGBP and is taken from Looger L. L. et al., *Nature* 423: 185-190, (2003), which herein incorporated by reference.

TABLE II

Mutations of GGBP residues providing L-lactate selectivity

| | Residue: | | | | | | | | | |
|---|---|---|---|---|---|---|---|---|---|---|
| | 10 | 14 | 16 | 91 | 92 | 152 | 154 | 158 | 183 | 236 | 256 |
| Wildtype GGBP | Y | D | F | N | K | H | D | R | W | D | N |
| Lactate-specific mutant G1 | K | K | F | K | L | M | H | K | K | A | D |
| Lactate-specific mutant G2 | K | M | K | K | L | K | K | M | K | A | S |

Derivative proteins or polypeptides of the present invention may be made or prepared by techniques well known to those of skill in the art. Examples of such techniques include, but are not limited to, mutagenesis and direct synthesis.

Derivative proteins may also be modified, either by natural processes, such as post-translational processing, or by chemical modification techniques which are well known in the art. Such modifications are well described in basic texts and in more detailed monographs, as well as in voluminous research literature. Modifications can occur anywhere in the polypeptide chain, including the peptide backbone, the amino acid side-chains and the amino or carboxyl termini. It will be appreciated that the same type of modification may be present in the same or varying degrees at several sites in a given polypeptide or protein. Also, a given polypeptide or protein may contain more than one modification. Examples of modifications include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Polypeptides or proteins may even be branched as a result of ubiquitination, and they may be cyclic, with or without branching. (See, e.g., T. E. Creighton, *Proteins—Structure And Molecular Properties,* 2nd Ed., W. H. Freeman and Company, New York (1993); Wold, F., "Posttranslational Protein Modifications: Perspectives and Prospects", in *Posttranslational Covalent Modification Of Proteins,* B. C. Johnson, Ed., Academic Press, New York (1983); Seifter et al., *Methods in Enzymol,* 182:626-646 (1990) and Rattan et al., *Ann NY Acad Sci.,* 663:48-62 (1992), all of which are incorporated herein by reference.

Examples of mutations of a GGBP protein, for example the GGBP protein of GenBank Accession No. P02927 without the 23 amino acid leader sequence (i.e., the mature chain), include, but are not limited to, having a cysteine substituted for lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for glycine at position 74 (G74C), a cysteine substituted for tyrosine at position 107 (Y107C), a cysteine substituted for threonine at position 110 (T110C), a cysteine substituted for serine at position 112 (S112C), a double mutant including a cysteine substituted for serine at position 112 and serine substituted for leucine at position 238 (S112C/L238S), a cysteine substituted for lysine at position 113 (K113C), a cysteine substituted for lysine at position 137 (K137C), a cysteine substituted for glutamic acid at position 149 (E149C), a double mutant including a cysteine substituted for glutamic acid at position 149 and an arginine substituted for alanine at position 213 (E149C/A213R), a double mutant including a cysteine substituted for glutamic acid at position 149 and a serine substituted for leucine at position 238 (E149C/L238S), a double mutant including a serine substituted for alanine at position 213 and a cysteine substituted for histidine at position 152 (H152C/A213S), a cysteine substituted for methionine at position 182 (M182C), a cysteine substituted for alanine at position 213 (A213C), a double mutant including a cysteine substituted for alanine at position 213 and a cysteine substituted for leucine at position 238 (A213C/L238C), a cysteine substituted for methionine at position 216 (M216C), a cysteine substituted for aspartic acid at position 236 (D236C), a cysteine substituted for leucine at position 238 (L238C) a cysteine substituted for aspartic acid at position 287 (D287C), a cysteine substituted for arginine at position 292 (R292C), a cysteine substituted for valine at position 296 (V296C), a triple mutant including a cysteine substituted for glutamic acid at position 149 and a serine substituted for alanine at position 213 and a serine substituted for leucine at position 238 (E149C/A213S/L238S), a triple mutant including a cysteine substituted for glutamic acid at position 149 and an arginine substituted for alanine at position 213 and a serine substituted for leucine at position 238 (E149C/A213R/L238S), a cysteine substituted for glutamic acid at position 149 and a cysteine substituted for alanine at position 213 and a serine substituted for leucine at position 238 (E149C/A213C/L238S). Additional embodiments include mutations of GGBP at Y10C, N15C, Q26C, E93C, H152C, M182C, W183C, L255C, D257C, P294C, and V296C.

Additional examples are mutations of maltose binding protein include, but are not limited to, D95C, F92C, I329C, S233C, and S337C.

Additional examples of mutations for histidine binding proteins include, but are not limited to, E167C, K229C, V163C, Y230C, F231C, and Y88C.

Additional examples of mutations' of the sulfate-binding protein including, for example, L65C, N70C, Q294C, R134C, W290C, and Y67C.

Additional examples of mutations to arabinose-binding protein include, but are not limited to D275C, F23C, K301C, L253C, and L298C.

Additional examples of mutations to dipeptide-binding protein include, but are not limited to D450C, K394C, R141C, S111C, T44C, and W315C.

Additional examples of mutations of glutamic acid/aspartic acid-binding protein include but are not limited to, A207C, A210C, E 119C, F126C, F131C, F270C, G211C, K268C, Q123C, and T129C.

Additional examples of mutations of glutamine-binding protein include, but are not limited to, N160C, F221C, K219C, L162C, W220C, Y163C, and Y86C.

Additional examples of mutations of Fe(III)-binding protein include, but are not limited to, E203C, K202C, K85C, and V287C.

Additional examples of mutations of ribose-binding protein include but are not limited to, T135C, D165C, E192C, A234C, L236C, and L265C.

Additional examples of mutations of phosphate-binding protein include but are not limited to, A225C, N223C, N226C, S164C, S39C, and A197C.

The mutation may serve one or more of several purposes. For example, a naturally occurring protein may be mutated in order to change the long-term stability, including thermal stability, of the protein, to conjugate the protein to a particular encapsulation matrix or polymer, to provide binding sites for detectable reporter groups, to adjust its binding constant with respect to a particular analyte, or combinations thereof.

In one embodiment, analyte and mutated protein act as binding partners. The term "associates" or "binds" as used herein refers to binding partners having a relative binding constant (Kd) sufficiently strong to allow detection of binding to the protein by a detection means. The Kd may be calculated as the concentration of free analyte at which half the protein is bound, or vice versa. When the analyte of interest is glucose, the Kd values for the binding partners are between about 0.0001 mM and about 50 mM.

Besides changing binding characteristics, derivative polypeptides or proteins are also used to incorporate a labeling moiety onto or within the binding entity or domain, such that the binding entities, e.g., polypeptides or proteins, comprising the binding domains may be labeled with a labeling moiety. Accordingly, in one embodiment of the present invention, all of the binding entities, comprising the binding domains, are labeled. In another embodiment, less than all, but at least one of the binding entities are labeled. In yet another embodiment, none of the binding entities are labeled. When some or all of the binding entities are labeled, there can be one labeling moiety per binding entity, or there can be more than one labeling moiety per binding entity.

The labels used in the present invention are used to indicate a change in the binding domains. Examples of changes in binding domains include, but are not limited to, three-dimensional conformational changes, changes in orientation of the amino acid side chains of proteinaceous binding domains, and redox states of the binding domains. With the addition/substitution of one or more residues into the primary structure of a protein, some of the labeling moieties used in the current methods and compositions can be attached through chemical means, such as reduction, oxidation, conjugation, and condensation reactions. Examples of residues commonly used to label proteins include, but are limited to, lysine and cysteine. For example, any thiol-reactive group can be used to attach labeling moieties, e.g., a fluorophore, to a naturally occurring or engineered cysteine in the primary structure of the polypeptide. Also, for example, lysine residues can be labeled using succinimide ester derivatives of fluorophores. See Richieri, G. V. et al., *J. Biol. Chem.*, 267: 23495-501 (1992) which is hereby incorporated by reference.

A "labeling moiety," as used herein, is intended to mean a chemical compound or ion that possesses or comes to possess a detectable non-radioactive signal. Examples of labeling moieties include, but are not limited to, transition metals, lanthanide ions and other chemical compounds. The non-radioactive signals include, but are not limited to, fluorescence, phosphorescence, bioluminescence, electrochemical and chemiluminescence.

In one embodiment of the present invention, the binding entities collectively comprise at least one label, which is a fluorophore. Examples of flurphores include, but are not limited to fluorescein, coumarins, rhodamines, 5-TMRIA (tetramethylrhodamine-5-iodoacetamide), o-aminobenzoic acid (ABZ), dinitrophenyl (DNP), 4-[(4-dimethylamino)phenyl]-azo)benzoic acid (DANSYL), 5- or 5(6)-carboxyfluorescein (FAM), 5- or 5(6)carboxytetramethylrhodamine (TMR), 5-(2-aminoethylamino)-1-naphthalenesulfonic acid (EDANS), 4-(dimethylamino)azobenzene-4'-carboxylic acid (DABCYL), 4-(dimethylamino)azobenzene-4'-sulfonyl chloride (DABSYL), nitro-Tyrosine (Tyr($NO_2$)), Quantum Red™, Texas Red™, Cy3™, 7-nitro-4-benzofurazanyl (NBD), N-((2-iodoacetoxy)ethyl)-N-methyl)amino-7-nitrobenzoxadiazole (IANBD), 6-acryloyl-2-dimethylaminonaphthalene (acrylodan), pyrene, Lucifer Yellow, Cy5™, Dapoxyl® (2-bromoacetamidoethyl)sulfonamide, (N-(4,4-difluoro-1,3,5,7-tetramethyl-4-bora-3a,4a-diaza-s-indacene-2-yl)iodoacetamide (Bodipy® 507/545 IA), N-(4,4-difluoro-5,7-diphenyl-4-bora-3a,4a-diaza-s-indacene-3-propionyl)-N'-iodoacetylethylenediamine (BODIPY® 530/550 IA), 5-((((2-iodoacetyl)amino)ethyl)amino)naphthalene-1-sulfonic acid (1,5-IAEDANS), carboxy-X-rhodamine, 5/6-iodoacetamide (XRIA 5,6), eosin, acridine orange, Alexa Fluor 350™, Alexa Fluor 405™, Alexa Fluor 430™, Alexa Fluor 488™, Alexa Fluor 500™, Alexa Fluor 514™, Alexa Fluor 532™, Alexa Fluor 546™, Alexa Fluor 555™, Alexa Fluor 568™, Alexa Fluor 594™, Alexa Fluor 610™, Alexa Fluor 633™, Alexa Fluor 635™, Alexa Fluor 647™, Alexa Fluor 660™, Alexa Fluor 680™, Alexa Fluor 700™ and Alexa Fluor 750™. Other luminescent labeling moieties include lanthanides such as europium (Eu3+) and terbium (Tb3+), as well as metal-ligand complexes of ruthenium [Ru(II)], rhenium [Re(I)], or osmium [Os(II)], typically in complexes with diimine ligands such as phenanthroline. In one particular embodiment of the current invention, there is one labeling moiety per binding domain, and the labeling moieties are acrylodan, NBD and Alexa Fluor 660™. In particular, a FABP is labeled with acrylodan, a GGBP or GGBP derivative specific for glucose is labeled with NBD and a GGBP derivative specific for L-lactate is labeled with Alexa Fluor 660™. Acrylodan-labeled FABP is commercially available (FFA Sciences, LLC, San Diego, Calif.) as "ADIFAB." A number of binding proteins, comprising biding domains, that are labeled with fluorescent labeling moieties are disclosed in de Lorimier, R. M. et al., *Protein Science* 11: 2655-75, (2002), which is herein incorporated by reference.

The fluorescent label can be attached to the mutated protein, for example a GGBP, by any conventional means known in the art. For example, the reporter group may be attached via amines or carboxyl residues on the protein. Exemplary embodiments include covalent coupling via thiol groups on cysteine residues of the mutated or native protein. For example, for mutated GGBP, cysteines may be located at position 10, at position 11, position 14, at position 15, position 19, at position 26, at position 43, at position 74, at position 92, at position 93, position 107, position 110, position 112, at position 113, at position 137, at position 149, at position 152, at position 154, at position 182, at position 183, at position 186, at position 211, at position 213, at position 216, at position 238, at position 240, at position 242, at position 255, at position 257, at position 287, at position 292, at position 294, and at position 296.

Any thiol-reactive group known in the art may be used for attaching labeling moieties such as fluorophores to the cysteine in a natural or an engineered or mutated protein. For example, iodoacetamide, bromoacetamide, or maleimide are well known thiol-reactive moieties that may be used for this purpose.

Labels, however, are not always necessary to indicate changes in the binding domains. For example, in surface plasmon resonance (SPR) an unlabeled binding entity comprising a binding domain, such as a protein, can be used to detect the presence or absence of a target analyte. Accordingly, in one embodiment of the present invention, the binding domains are not labeled.

The devices of the present invention also comprise a membrane surrounding the binding domains. In one embodiment, each individual binding domain is surrounded by a membrane. In another embodiment, more than one of the binding domains are surrounded by a single membrane. In yet another embodiment, all the binding domains of the device are surrounded by a single membrane. The present invention encompasses several alternative, but not necessarily mutually exclusive, embodiments of configuring the devices for concurrent detection of multiple analytes include, but are not limited to: (1) a plurality of labeled binding domains within a single membrane and single device with a single excitation wavelength and detection of multiple luminescence emission wavelength intensities; (2) a plurality of labeled binding domains within a single membrane and device with multiple excitation wavelengths and detection of multiple luminescence emission wavelength intensities; (3) a plurality of labeled binding domains within a membrane and device with a single excitation wavelength and detection of multiple luminescence lifetimes; (4) a plurality of labeled binding domains within a plurality of membranes in a device with a single excitation wavelength and detection of a plurality of luminescence emission wavelength intensities; (5) a plurality of labeled binding domains within a plurality of membranes in a device with a plurality of excitation wavelengths and detection of a plurality of emission wavelength intensities; (6) a plurality of labeled binding domains within a plurality of membranes in a device with a single excitation wavelength and detection of a plurality of luminescence lifetimes; (7) a plurality of devices, each with a labeled binding domain and membrane, at the same excitation wavelength and detection of luminescence emission from each device at the same wavelength; (8) a plurality of devices, each with a labeled binding domain and membrane, at the same excitation wavelength and detection of luminescence lifetime.

The membranes must be permeable to the target analytes. The membrane should also have at least some degree of hydrophobicity, such that the membrane(s) will mimic, at least partially, a cell membrane. The membranes can serve to indirectly immobilize the binding domains, when the binding domains are not directly immobilized themselves.

The membranes can be made of naturally occurring lipids, such as phospholipids that primarily compose normal cell membranes. Examples of classes of lipids of which the membranes may comprise include, but are not limited to, fatty acids, triacylglycerols, phospholipids, sphingolipids, steroids and cholesterol. In one embodiment, the membrane comprises one or more phospholipids. In particular, the phospholipids are phosphatidylcholine, phosphatidylethanolamine, phosphatidylserine or combinations thereof.

The phospholipids used in the membranes also include, but are not limited to, phospholipids containing saturated or unsaturated mono or disubstituted fatty acids and combinations thereof. Examples of such phospholipids include, but are not limited to, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolam ine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylchol ine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophosphatidylidylcholine), phosphatidylserine (lysophosphatidylserine), phosphatidylethanolamine(lysophosphatidylethanolamine), phophatidylglycerol(lysophosphatidylglycerol) and phosphatidic acid (lysophosphatidic acid). The monoacyl chain in these lysophosphatidyl derivatives may be palmitoyl, oleoyl, palmitoleoyl, linoleoyl myristoyl or myristoleoyl.

An example of membranes that are comprised of lipids includes liposomes. Liposomes are a general category of vesicles which comprise one or more lipid bilayers surrounding an aqueous space. Liposomes include unilamellar vesicles composed of a single membrane or lipid bilayer, and multilamellar vesicles composed of more than one concentric membrane (or lipid bilayer). Liposomes are commonly prepared from phospholipids and may also comprise fatty acids, such as oleic acid, proteins or polypeptides and other molecules, such as cholesterol. Techniques for preparing liposomes and encapsulating molecules, such as proteins, within liposomes are well-known in the art. See "Bioconjugate Techniques", G. T. Hermanson, Academic Press, San Diego, Calif. (1996), pp. 531-533, which is hereby incorporated by reference.

Another example of a membrane that could surround the binding domains is a Langmuir-Blodgett film. Langmuir-Blodgett films (LB films) are mechanically assembled arrays of amphiphillic molecules, such as fatty acids that are deposited on a solid substrate. LB films may, however, comprise other molecules, including inorganic molecules. LB films can easily be assembled by one of skill in the art. See B. D. Ratner and A. S. Hoffmann, "Thin Films, Grafts, and Coatings" Chapter 2, in "Biomaterials Science: An Introduction to Materials in Medicine", B. D. Ratner, A. S. Hoffman, F. J. Shoen, J. E. Lemons, editors, Academic Press, San Diego, Calif., 1996. The entirety of"Biomaterials Science: An Introduction to Materials in Medicine" is herein incorporated by reference.

The membrane(s) may also comprises a polymer. Examples of polymers of which the membrane my comprise include, but are not limited to, vinyl alcohol, acrylamide, N-vinyl pyrolidone, ethylene oxide, hydrolysed acrylonitrile, acrylic acid, methacrylic acid, hydroxyethyl methacrylate (HEMA), methyl methacrylate (MMA), urethane, ethylene amine, ethylene glycol, methacrylate-phosphorylcholine (MPC), lauryl methacrylate (LMA), tetramethyl orthosilicate, tetraethyl orthosilicate, cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof. For example, in one embodiment of the present invention, the membrane comprises the polymers methacrylate-phosphorylcholine and lauryl methacrylate. In particular, this embodiment would also comprise hydroxyethyl methacrylate and/or methyl methacrylate to modulate overall charge and hydrophobicity of the membrane, as well as to modify other properties that may affect cross-linking and protein immobilization.

In one embodiment of the present invention, the membrane is used to surround and immobilize the binding domains. For example, a hydrogel of poly(ethylene glycol), poly(acrylamide), poly(acrylates) and/or teraalkylammonium can be produced wherein the biding domains are either physically entrapped in and surrounded by the hydrogel, or the domains are covalently attached to and surrounded by the hydrogel. The constituents of the hydrogel membranes could be modified to change the hydrophobicity and charge of the hydrogel, for example, if necessary.

Regardless of the constituents of the surrounding membrane, the surrounding membrane can be used to establish an artificial cell membrane that can be useful in establishing an equilibrium between the two sides of the membrane, similar to a cell membrane. For example, it has been shown that changes in intracellular pH results in passive FFA movement across a cell membrane. (See Civelek, V. N. et al., *Proc. Nat'l. Acad. Sci.*, 93:10139-10144 (1996), which is hereby incorporated by reference.) Accordingly, the membranes used in the devices of the present invention may be used to establish and maintain an interior pH that can facilitate diffusion of FFA, or other target analytes across the membrane. The membranes may be used to establish other physiologically relevant features, such as isoelectric potentials and concentration gradients that can also foster diffusion across the membrane to mimic cellular conditions. By adjusting concentration gradients, the response of a given binding domain can be modified to respond to a specific analyte concentration range, especially a range equivalent to physiological or disease-specific analyte concentrations.

The devices of the present invention must be able to convey a signal to a detector that can detect the signal. In one embodiment of the present invention, the device further comprises the signal detector. In another embodiment, the device does not comprise the signal detector. The generated signal is a direct indication of the binding of the target analytes to the binding domains. In other words, the binding of the target analytes to the binding domain either creates or alters the quality of a signal that is discernable using a detector. Changes in signal quality include, but are not limited to, light wavelength shift and signal intensity. In one embodiment, the binding domains do not generate a signal when not bound to the target analytes. In another embodiment, the binding domains generate a signal, even when not bound to a target analyte, but the binding of the target analyte, however, still changes the quality of the signal, such that binding is discernable. It is also certainly possible that the binding of the target analyte to the binding domain may cause a decrease in signal intensity, simply provided that the alteration in the signal is discernable to the detector.

In one embodiment of the current invention, the detector is a fluorometer that can measure the wavelength and/or intensity of fluorescent light. Examples of other detectors can be an infrared spectrophotometer, a UV-Vis spectrophotometer, a photodiode that can be used in surface plasmon resonance (SPR) protocols and even the naked eye. In SPR, the refractive index properties of a sample near a surface will change when the target molecule is present, and the intensity of the reflected light is dampened by the presence of a metal surface at the interface of the sample and glass media. The decrease in intensity occurs at a well-defined angle, which is dependent on the refractive indices of the two media, referred to as the "resonance angle."

The devices of the current invention can be used in a variety of settings, including in vivo, in vitro and in situ. In one embodiment of the present invention, the devices are medical devices or implants. When the implants are used in an in vivo setting, the implants should be biocompatible such that they produce little or no detectable inflammation/rejection reaction. One embodiment for rendering the implants more biocompatible comprises coating the implants with biocompatible polymers, such as poly(urethane) elastomers, poly(urea) and poly(vinylchloride). Poly(urethane) elastomers posses excellent mechanical properties including high tensile strength, good tear and abrasion resistance and a relatively good stability in biological environments. The excellent mechanical properties of segmented polyurethanes are attributed to their two phase morphology derived from microphase separation of soft and hard segments. When polyurethanes are used for long term medical implants, the soft segments are typically formed from a poly(ether) macrodiol such as poly(tetramethylene oxide) (PTMO), whereas the hard segments are derived from a diisocyanate such as 4,4'-methylenediphenyl diisocyanate (MDI) and a diol chain extender such as 1,4-butanediol. Other coatings of the implant may include poly(urea) compositions disclosed in U.S. Pat. No. 6,642,015, which is hereby incorporated by reference. Other formulations for rendering the implant biocompatible are disclosed in U.S. Pat. No. 6,706,532, which is hereby incorporated by reference. Additionally, Quinn et al., (Biomaterials, 18: 1665-1670 (1997)), which is herein incorporated by reference, reports an amperometric glucose electrode biosensor constructed with poly(ethylene glycol) (PEG) hydrogels as an outer layer to provide biocompatibility for enzymatic biosensors.

The present invention relates to methods of monitoring metabolic substrate levels in a subject comprising implanting the sensor into the subject. The terms "subject" and "patient" are used interchangeably herein. As used herein, a the term "subject" is used to mean an animal, in particular a mammal, and even more particularly a non-human and human primate. The implants could be designed to simultaneously monitor a variety of metabolites, the measurements of which could be used to profile the subject's metabolic or physical state. For example, during extended periods of strenuous exercise, glucose is broken down in anaerobic processes to lactic acid. The biosensors are useful in determining lactate thresholds of athletes, to maximize the benefits of training and decrease recovery time. Similarly, the biosensors are useful for in determining lactate thresholds in soldiers, to prevent fatigue and exhaustion and to decrease recovery time. To that end, the sensors of the current invention are useful in monitoring glucose levels, lactic acids levels and other metabolites during exercise or physical stress.

The present invention also relates to methods of monitoring disease states in a subject. In one embodiment, of the present invention, the diseases monitored are chronic diseases, such as, but not limited to, heart disease, coronary artery disease, diabetes, metabolic disorders, inflammatory diseases, such as rheumatoid arthritis and cancer. The various metabolic disorders include, but are not limited to, hyperlipidemia, hypolipidemia, hyperthyroidism, hypothyroidism.

The present invention also relates to monitoring patients is acute care facilities, such as an emergency room or a post-operative recovery room or a hospital. Studies have shown that mortality can be decreased by as much as 30% in post-operative patients, when glucose levels are monitored and kept normal. Thus the multianalyte biosensor of the present invention may used in situations where monitoring glucose is or other metabolites is essential to recovery or the overall health of the subject.

The implants are designed to monitor specific markers of the chronic disease. By monitoring the concentrations of molecular artifacts and deleterious and/or beneficial molecules of the disease state, the subjects progression, regression or stability can be readily assessed, and treatments can, in turn be adjusted or revised accordingly. Accordingly, the methods of the current invention relate to methods of treating subjects in need of treatment thereof, comprising the use of the biosensors of the present invention.

For example, markers heart disease that could be monitored in vivo using the biosensors include, but are not limited to, total fatty acids, lactate, glucose, free fatty acids and various cardiotonic agents such as, but not limited to cardioglycosides and sympathomimetics. The marker of diabetes, for example, include, but are not limited to, glucose, lactate and fatty acids. The markers for coronary artery disease may include, but are not limited to, C-reactive peptide and free fatty acids. The markers of various metabolic disorders include, but are not limited to specific fatty acids. When monitoring the concentrations of specific fatty acids, the binding domains should be specific for individual fatty acid species.

As alluded to earlier, the present invention also relates to methods of monitoring drug treatment. Indeed, the biosensor could be designed to specifically bind a drug, drug candidate or a drug metabolite. In this manner, the plasma concentration of the drug could be monitored and dosages could be adjusted or maintained based on the concentration measurements provided by the sensor. Thus, in one embodiment of the present invention, the invention relates to a method of individualizing a pharmaceutical regimen to a subject comprising implanting a biosensor that can specifically and reversibly bind the drug or drug metabolite to determine plasma concentrations of the drug. The concentrations provided by the sensor can then be used to determine the bioavailability of the drug in the subject. The dose of the drug administered to the subject may then be altered to increase or decrease the bioavailability of the drug to the subject to provide maximum therapeutic benefits and avoiding toxicity.

EXAMPLES

Example 1

Hydrogel Glucose Biosensor on an Optical Fiber

This example illustrates the use of a hydrogel with binding protein coated on an optical fiber as a device for continuous monitoring glucose concentration in vitro and in vivo. A solution of 25.7 mg of 8-arm PEG-NH2 in 0.3 mL PBS buffer (pH 7.4) in a 1.5 mL Eppendorf vial was mixed with 200 uL of NBD-labeled E149C/A231R/L238S GGBP in PBS buffer (protein concentration is 125.5 uM with dye/protein ratio 0.9). The NBD-labeled E149C/A231R/L238S GGBP was prepared as described in U.S. application Ser. No. 10/040,077, filed Jan. 4, 2002, which is incorporated herein by reference. Next, 24.5 mg of BTC-PEG-BTC in 0.5 mL PBS buffer was added to the mixture. After thorough mixing, the final mixture was manually coated onto the end of a 470 um optical fiber (Ceram Optec, East Longmeadow, Mass.), and the reaction was allowed to continue for at least two hours. The gel formed within a few minutes and formed very thin hydrogel films with a thickness of about 100 to about 500 µm on the optical fiber tip. Because PEG is a hydrophilic polymer, it can form strong hydrogen bonds with the hydroxyl groups on the surface of the silica core of the fiber tip.

Figure 2:
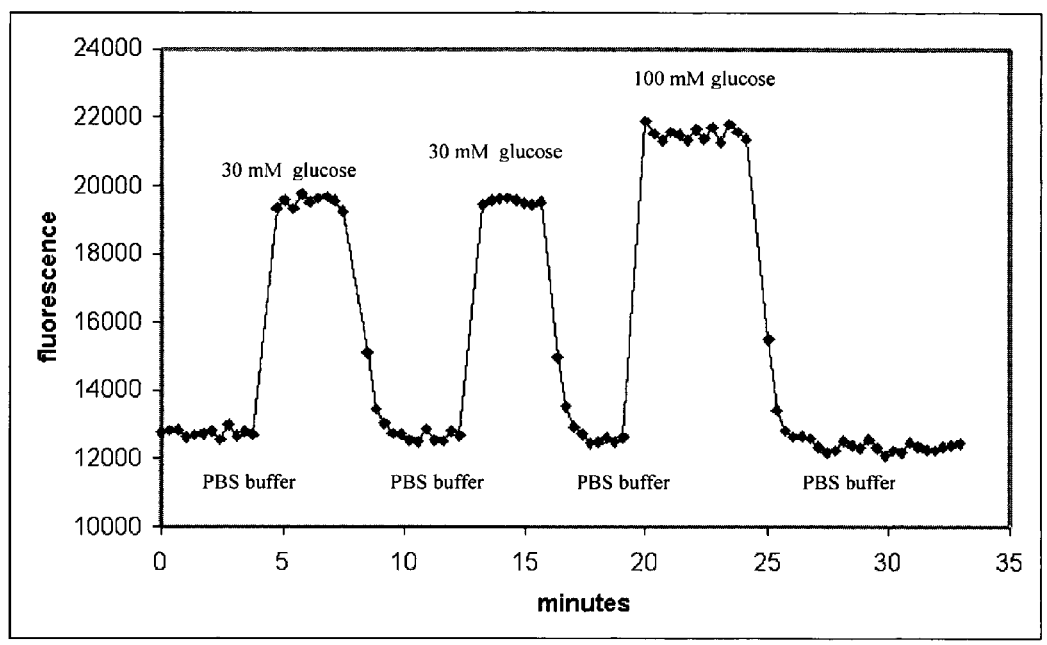
FIG. 2 depicts a graph showing the response time of a biosensor of the present invention in response to varying concentrations of glucose.

The hydrogel biosensor was used to continuously monitor glucose concentration changes using a custom fluorometer. An example of a fluorometer is described in U.S. application Ser. No. 10/721,797, filed Nov. 26, 2003, which is hereby incorporated by reference. The fluorometer was equipped with a 470 nm LED light source and a dichroic filter to reflect the 470 nm excitation towards the input end of the fiber and to transmit the fluorescence from the fiber towards a 550 nm bandpass filter leading to a single photon counting photomultiplier tube detector. Glass aspheric lenses were used both for beam collimation and to focus light into the fibers and onto the detectors. FIG. 2 depicts the fluorescence response of the fiber optic sensor following its immersion into solutions of the indicated glucose concentrations (0, 30, and 100 mM glucose). Due to the thinness of the biosensor, glucose was able to permeate to the hydrogel matrix quickly, and the sensor reached an apparent equilibrium within approximately one minute, demonstrating that the sensor can be used to monitor glucose concentration changes in real time.

Figure 3:
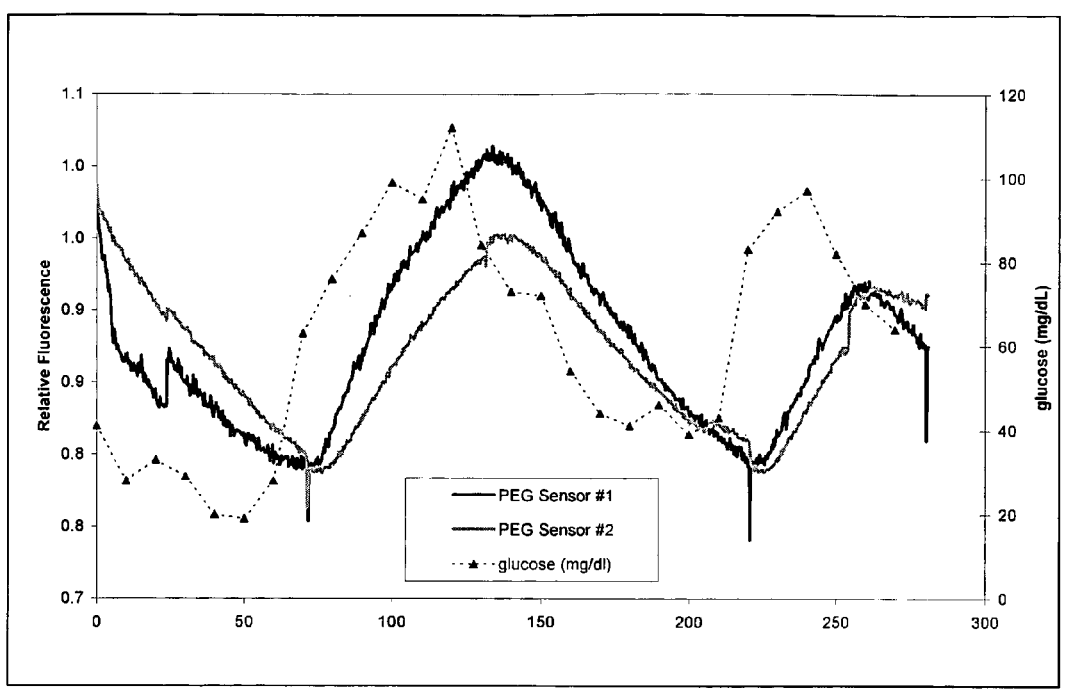
FIG. 3 depicts a graph tracking the changes in glucose concentration in vivo in a pig using the hydrogel biosensors of the present invention.

Additional hydrogel biosensors were fabricated using the general procedures described above, except that the optical fibers were glued inside 21 gauge needles, and hydrogels were coated on the fiber tips to completely fill the needle bevels. The sensors were used to track in vivo glucose concentration changes in a pig. Two fiber optic sensors were inserted into the side of an anesthetized pig. Alternating solutions of lactated ringer's solution, with and without 10% dextrose, were infused through the ear vein of the pig to increase and decrease glucose levels in a controllable fashion. At ten minute intervals, blood samples were pulled from the vena cava of the pig through a chest catheter, and blood sugar readings were tested on a handheld blood glucose meter. The fluorescence intensity of the two biosensors was observed to track changing blood glucose levels in the anesthetized pig as shown in FIG. 3.

Example 2

Fatty Acid Binding Protein Immobilized in a PEG Hydrogel

Figure 4:
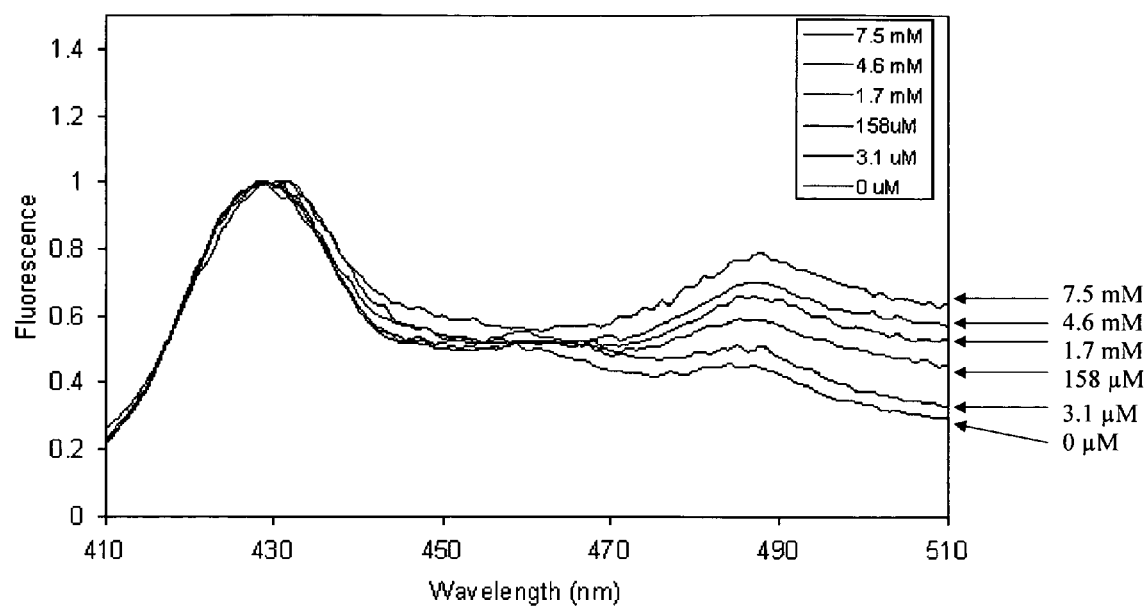
FIG. 4 depicts a graph showing the response to varying concentrations of fatty acid by a hydrogel biosensor.

This example describes making hydrogel biosensors for fatty acid detection. A solution of 200 ug of ADIFAB (AcryloDated Intestinal Fatty Acid Binding Protein with dye/protein ratio approximately 1.0, Molecular Probes) in 1.0 mL of buffer (50 mM Tris, 1 mM EDTA, 0.05% azide, pH 8.0) was prepared. The binding protein solution (210 uL) was combined with 21 mg of 8-arm PEG-NH2 (10,000 MW, Nektar) in a 1.5 mL Eppendorf vial. The mixture of 8-arm PEG-NH2 and binding protein was further mixed with 18 mg of BTC-PEG-BTC (3,400 MW, Nektar) in 180 uL PBS buffer (pH 7.4) and vortexed. The mixture was immediately injected between two glass plates separated by a 2 mm spacer. After the reaction was complete, the formed hydrogel sheet was punched into 5 mm diameter disks, which were then soaked in PBS buffer for two days to wash away unbound protein and monomer residuals. The binding of fatty acid to the hydrogel disks was measured using a Varian Cary Eclipse fluorometer and 96 well plates (excitation was at 390 nm). FIG. 4 depicts the fluorescence response of the hydrogel disks to a wide range of arachadonic acid concentrations. The hydrogel sensor responded to FA (fatty acid, e.g., arachadonic acid) with a shift of fluorescence emission wavelength from 432 nm to 486 nm. Increasing FA concentration caused an increase in the emission intensity at 486 nm.

Example 3

Multianalyte Hydrogel Biosensor on an Optical Fiber for Detection of Glucose and Lactate This example illustrates the use of a hydrogel with two binding proteins coated on an optical fiber as a device for simultaneous monitoring of glucose and L-lactate. An NBD-labeled GGBP derivative is used to monitor glucose and an acrylodan-labeled GGBP derivative with mutations for selective lactate binding is used to monitor L-lactate. A solution of 25.7 mg of 8-arm PEG-NH$_2$ in 0.3 mL PBS buffer (pH 7.4) in a 1.5 mL Eppendorf vial is mixed with a 200 uL 1:1 equimolar mixture (approximately 50-65 uM each) of (1) NBD-labeled glucose-specific GGBP mutant E149C/A231R/L238S, and (2) Acrylodan-labeled lactate-specific GGBP mutant Y10K/D14K/N91K/K92L/E149C/H152M/D154H/R158K/W183K/D236A/N256D in PBS buffer. Next, 24.5 mg of BTC-PEG-BTC in 0.5 mL PBS buffer is added to the mixture. After thorough mixing, the final mixture is manually coated onto the end of a 470 um optical fiber (Ceram Optec, East Longmeadow, Mass.), and the reaction is allowed to continue for at least two hours. The hydrogel biosensor is used to continuously monitor glucose and lactate concentration changes using a fluorometer. Excitation at 390 nm and measurement of emission through a narrow bandpass filter at approximately 515 nm provides a signal corresponding to the presence and concentration of L-lactate. Excitation at 475 nm and measurement of emission through a bandpass filter at approximately 550 nm provides a signal corresponding to the presence and concentration of glucose.

What is claimed is:
1. A device for measuring the concentrations of more than one target analyte, said device comprising
   a) more than one set of fluorescently labeled binding proteins, wherein each set of said fluorescently labeled binding proteins is capable of specifically and reversibly binding to one of said target analytes said target analytes being unlabeled; and b) a membrane surrounding said more than one set of fluorescently labeled binding proteins, said membrane being permeable to said unlabeled target analytes;

said device being capable of conveying to a fluorescence detector a shift in the fluorescence signal emitted from the fluorescent label upon binding of said unlabeled target analytes to said fluorescently labeled binding proteins, wherein the number of sets of fluorescently labeled binding proteins corresponds to the number of different analytes detected.

2. The device of claim 1, wherein said device is capable of continuously conveying to a detector the presence or absence of binding of said target analytes to said binding domains.

3. The device of claim 1, wherein said target analytes are selected from the group consisting of amino acids, peptides, polypeptides, proteins, carbohydrates, lipids, nucleotides, oligonucleotides, polynucleotides, glycoproteins, proteoglycans, lipoproteins, drugs, drug metabolites, small organic molecules, inorganic molecules, polymers and combinations thereof.

4. The device of claim 3, wherein one of said target analytes is selected from the group consisting of fatty acids, lactate and glucose.

5. The device of claim 4, wherein said target analytes are at least two of fatty acids, lactate or glucose.

6. The device of claim 5, wherein at least of one of said one or more polypeptides or proteins are selected from the group consisting of galactose/glucose binding protein (GGBP), maltose binding protein (MBP), ribose binding protein (RBP), arabinose binding protein (ABP), dipeptide binding protein (DPBP), glutamine binding protein (QBP), iron binding protein (FeBP), histidine binding protein (HBP), phosphate binding protein (PhosBP), oligopeptide binding protein (OppA) and a fatty acid binding protein (FABP) and derivatives thereof.

7. The device of claim 6, wherein said one or more polypeptides or proteins are GGBP, a FABP and a GGBP derivative.

8. The device of claim 7, wherein said target analytes are at least two selected from the group consisting of glucose, fatty acids and lactate.

9. The device of claim 8, wherein said at least two analytes are glucose and fatty acids.

10. The device of claim 8, wherein said at least two analytes are glucose and lactate.

11. The device of claim 10, wherein said membrane comprises a lipid.

12. The device of claim 11, wherein said lipid is a glycerophospholipid.

13. The device of claim 12, wherein said glycerophospholipid is selected from the group consisting of a phosphatidylcholine, a phosphatidylethanolamine, a phosphatidylserine 14. The device of claim 10, wherein said membrane comprises a polymer.

15. The device of claim 14, wherein said polymer comprises a compound selected from the group consisting of polyvinyl alcohol, polyacrylamide, polyN-vinyl pyrolidone, polyethylene oxide, polyhydrolysed acrylonitrile, polyacrylic acid, polymethacrylic acid, polyhydroxyethyl methacrylate (polyHEMA), polymethyl methacrylate (polyMMA), polyurethane, polyethylene amine, polyethylene glycol, polymethacrylate-phosphorylcholine (polyMPC), polylauryl methacrylate (polyLMA), hydroxyethyl methacrylate-methyl methacrylate copolymer (polyHEMA-MMA), tetramethyl orthosilicate, tetraethyl orthosilicate, cellulose, cellulose acetate, carboxy methyl cellulose, alginic acid, pectinic acid, hyaluronic acid, heparin, heparin sulfate, chitosan, carboxymethyl chitosan, chitin, collagen, pullulan, gellan, xanthan, carboxymethyl dextran, chondroitin sulfate, cationic guar, cationic starch as well as salts and esters thereof.

16. A method of monitoring the metabolic substrate levels in a subject comprising implanting the device of claim 2 in said subject to allow measurement of said substrate levels, and collecting said measurements of said substrate levels.

17. A method of monitoring diabetes in a subject comprising implanting the device of claim 2 in said subject, wherein one of said target analytes is selected from the group consisting of fatty acids, lactate, and glucose.

18. The method of claim 16, wherein one of the target analytes is glucose.

* * * * *